US011613510B2

(12) United States Patent
White et al.

(10) Patent No.: US 11,613,510 B2
(45) Date of Patent: *Mar. 28, 2023

(54) METHYLCYCLOHEXANE AS ALLYL ALCOHOL HYDROFORMYLATION SOLVENT

(71) Applicant: Lyondell Chemical Technology, L.P., Houston, TX (US)

(72) Inventors: Daniel F. White, Houston, TX (US); Beaven S. Mandimutsira, Sugar Land, TX (US); Robert J. Rebman, Pearland, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/715,545

(22) Filed: Apr. 7, 2022

(65) Prior Publication Data

US 2022/0324782 A1 Oct. 13, 2022

Related U.S. Application Data

(60) Provisional application No. 63/172,763, filed on Apr. 9, 2021.

(51) Int. Cl.
| | |
|---|---|
| C07C 45/50 | (2006.01) |
| C07C 29/141 | (2006.01) |
| B01J 23/755 | (2006.01) |
| B01J 31/24 | (2006.01) |

(52) U.S. Cl.
CPC ........... *C07C 45/505* (2013.01); *B01J 23/755* (2013.01); *B01J 31/2409* (2013.01); *B01J 2231/321* (2013.01); *B01J 2531/822* (2013.01)

(58) Field of Classification Search
CPC ............................ C07C 45/505; C07C 29/141
See application file for complete search history.

(56) References Cited

U.S. PATENT DOCUMENTS

| | | | |
|---|---|---|---|
| 4,064,145 | A | 12/1977 | Taylor |
| 4,215,077 | A | 7/1980 | Matsumoto et al. |
| 4,238,419 | A | 12/1980 | Matsumoto et al. |
| 4,678,857 | A | 7/1987 | Dureanleau et al. |
| 5,290,743 | A | 3/1994 | Chang |
| 6,225,509 | B1 | 5/2001 | Dubner et al. |
| 7,271,295 | B1 | 9/2007 | White et al. |
| 7,279,606 | B1 | 10/2007 | White |
| 7,612,241 | B1 | 11/2009 | White et al. |
| 10,807,934 | B1 * | 10/2020 | White .................. C07F 9/5027 |

FOREIGN PATENT DOCUMENTS

WO       2020242977  A1    12/2020

OTHER PUBLICATIONS

The International Search Report and The Written Opinion for PCT/US2022/023845 dated Jul. 22, 2022.

* cited by examiner

*Primary Examiner* — Sikarl A Witherspoon

(57) ABSTRACT

A process for the production of 4-hydroxybutyraldehyde is described. The process comprises reacting allyl alcohol with a mixture of carbon monoxide and hydrogen in the presence of methylcyclohexane as a reaction solvent and a catalyst system comprising a rhodium complex and a substituted or unsubstituted diphosphine ligand. The use of the methylcyclohexane increases the reaction rate while also giving a high yield of 4-hydroxybutyraldehyde compared to 3-hydroxy-2-methylpropionaldehyde and improving the separation of the hydroxyaldehyde products from the catalyst system.

15 Claims, No Drawings

METHYLCYCLOHEXANE AS ALLYL ALCOHOL HYDROFORMYLATION SOLVENT

PRIOR RELATED APPLICATIONS

This application claims the benefit of priority to U.S. Provisional Patent Application No. 63/172,763, filed on Apr. 9, 2021, which is incorporated herein by reference in its entirety.

FEDERALLY SPONSORED RESEARCH STATEMENT

Not applicable.

REFERENCE TO MICROFICHE APPENDIX

Not applicable.

FIELD OF THE DISCLOSURE

The disclosure relates generally to the production of hydroxy compounds, and specifically to the hydroformylation of allyl alcohol to produce 4-hydroxybutyraldehyde.

BACKGROUND OF THE DISCLOSURE 1,4-butanediol (BDO) is an important raw material in manufacturing plastics, elastic fibers, and films. BDO is used as an intermediate in common industrial and commercial products such as polyether diols, urethane polymers and polyester polymers. Sizable quantities of BDO are also used to make gamma-butyrolactone (GBL), which finds use in electronics, pharmaceuticals, and agrochemicals, as well as high-performance polymers. This variety of applications has led to a high demand for BDO.

BDO can be produced in many ways. BDO can be derived from tetrahydrofuran, succinic acid, maleic anhydride and other four-carbon organic species, but such methods are not economically attractive. Another method of producing BDO is by the reaction of formaldehyde and acetylene to form 1,4-butynediol as an intermediate, which is subsequently hydrogenated to the desired BDO product. See, for example, U.S. Pat. Nos. 4,064,145; 4,215,077; 4,238,419; 4,678,857; 5,290,743, and 7,612,241.

A more economically attractive production method involves the hydroformylation of allyl alcohol. The hydroformylation of olefinic compounds in the presence of precious metal and phosphorus compound catalyst systems is well known. The hydroformylation of allyl alcohol yields 4-hydroxybutanal (HBA) as an intermediate which is subsequently hydrogenated to BDO. However, a disadvantage of the hydroformylation process is that other co-products or byproducts are also formed in addition to the desired HBA linear product. The hydroformylation of allyl alcohol produces some 3-hydroxy-2-methylpropionaldehyde (HMPA) branched co-product and C3 byproducts such as n-propanol and propionaldehyde (PA).

All of the aldehyde products have to be extracted from the hydroformylation product stream and hydrogenated. Although HMPA may be hydrogenated to produce 2-methyl-1,3-propanediol (MPD), which is a useful material, the MPD co-product reduces the yield of BDO from HBA. Formation of the C3 byproducts effectively represents another yield loss in the process which can have a severe adverse effect on the process economics. Further, there is a tendency for the hydrogenation catalyst, used to convert the aldehydes to hydroxy compounds, to deactivate with time.

Thus, there exists a need for improvements to the hydroformylation process to increase BDO yields while reducing less desired co-product/byproducts. Ideally, these improvements will also extend the life of the hydrogenation catalyst to further increase BDO production.

SUMMARY OF THE DISCLOSURE

The present disclosure is directed to an improved hydroformylation process to produce 4-hydroxybutyraldehyde. In particular, a hydroformylation process that utilizes a catalyst system combining a rhodium complex and a substituted or unsubstituted diphosphine ligand has been modified to use methylcyclohexane as a reaction solvent. This particular reaction solvent was found to unexpectedly increase the reaction rate of the hydroformylation process while maintaining a high yield of 4-hydroxybutyraldehyde compared to 3-hydroxy-2-methylpropionaldehyde. Further, the methylcyclohexane was found to be immiscible with the hydroxyaldehyde products, which reduces in the amount of water required in the subsequent extraction step, allowing for a larger recovery of desired products. These improvements result in cost savings for the process as less rhodium will be needed in the catalyst system and less water is needed for the extraction step.

The present methods include any of the following embodiments in any combination(s) of one or more thereof:

A process to produce 4-hydroxybutyraldehyde comprising reacting allyl alcohol with carbon monoxide and hydrogen in the presence of a methylcyclohexane reaction solvent and a catalyst system comprising a rhodium complex and a substituted or unsubstituted diphosphine ligand.

Any of the processes described herein, wherein the substituted or unsubstituted diphosphine ligand is trans-1,2-bis(bis(3,5-di-n-alkylphenyl)phosphinomethyl)-cyclobutane or 2,3-O-isopropylidene-2,3-dihydroxy-1,4-bis[bis(3,5-di-n-alkylphenyl)phosphino]-butane, wherein the n-alkyl group is a methyl, ethyl, or propyl.

Any of the processes described herein, wherein the substituted or unsubstituted diphosphine ligand is 4,5-bis(di-n-alkylphosphino)xanthene and the n-alkyl group is a C1-C6 group.

Any of the processes described herein, wherein the 4,5-bis(di-n-alkylphosphino)xanthene ligand is 9,9-dimethyl-4,5-bis(dimethylphosphino)xanthene.

Any of the processes described herein, wherein the 4,5-bis(di-n-alkylphosphino)xanthene ligand is 9,9-dimethyl-4,5-bis(diethylphosphino)xanthene.

Any of the processes described herein, wherein the 2,3-O-isopropylidene-2,3-dihydroxy-1,4-bis[bis(3,5-di-n-alkylphenyl)phosphino]-butane ligand is 2,3-O-isopropylidene-2,3-dihydroxy-1,4-bis[bis(3,5-dimethylphenyl)phosphino]butane.

Any of the processes described herein, wherein the 2,3-O-isopropylidene-2,3-dihydroxy-1,4-bis[bis(3,5-di-n-alkylphenyl)phosphino]-butane ligand is 2,3-O-isopropylidene-2,3-dihydroxy-1,4-bis[bis(3,5-diethylphenyl)phosphino]butane.

Any of the processes described herein, wherein the trans-1,2-bis(bis(3,5-di-n-alkylphenyl)phosphinomethyl)-cyclobutane is trans-1,2-bis(bis(3,5-di-methylphenyl)phosphinomethyl)-cyclobutane.

Any of the processes described herein, wherein the trans-1,2-bis(bis(3,5-di-n-alkylphenyl)phosphinomethyl)-cyclobutane is trans-1,2-bis(bis(3,5-di-ethylphenyl)phosphinomethyl)-cyclobutane.

Any of the processes described herein, wherein the rhodium complex comprises rhodium and one or more ligands selected from the group consisting of hydride, carbonyl, trialkyl or triaryl phosphines, diphosphines, cyclopentadienyls, 2,4-alkanedionates, and mixtures thereof.

Any of the processes described herein, wherein the reaction is performed at a temperature within the range of about 45° C. to about 85° C. and a pressure within the range of about 30 (~0.21 MPa) to about 400 psig (~2.76 MPa).

Any of the processes described herein, wherein the reaction is performed at a temperature within the range of about 65° C. to about 85° C. and a pressure within the range of about 200 psig (~1.37 MPa).

Any of the processes described herein, wherein the catalyst system further comprises a monophosphine compound.

Any of the processes described herein, wherein the monophosphine compound is triphenylphosphine.

Any of the processes described herein, wherein the concentration of carbon monoxide in the liquid phase is maintained in the range of from about 2 mmols/liter (0.002 M) to about 10 mmols/liter (0.010 M).

Any of the processes described herein, wherein the concentration of carbon monoxide in the liquid phase is maintained in the range of from about 3 mmols/liter (0.003 M) to about 6 mmols/liter (0.006M).

Any of the processes described herein, wherein the concentration of carbon monoxide in the liquid phase is maintained in the range of from about 4 mmols/liter (0.004M) to about 8 mmols/liter (0.008 M).

Any of the processes described herein, wherein the concentration of carbon monoxide in the liquid phase is maintained in the range of from about 4 mmols/liter (0.004M) to about 25 mmols/liter (0.025 M).

Any of the processes described herein, wherein the concentration of carbon monoxide in the liquid phase is maintained in the range of from about 4 mmols/liter (0.004M) to about 50 mmols/liter (0.050 M).

Any of the processes described herein, wherein the concentration of carbon monoxide in the liquid phase is maintained in the range of from about 4 mmols/liter (0.004M) to about 100 mmols/liter (0.100 M).

Any of the processes described herein, wherein the concentration of carbon monoxide in the liquid phase is maintained above 4 mmols/liter (0.004 M).

Any of the processes described herein, further comprising hydrogenating the 4-hydroxybutyraldehyde in the presence of a hydrogenation catalyst to form 1,4-butanediol.

Any of the processes described herein, wherein the hydrogenation catalyst is a nickel catalyst.

This summary is provided to introduce a selection of concepts that are further described below in the detailed description. This summary is not intended to identify key or essential features of the claimed subject matter, nor is it intended to be used as an aid in limiting the scope of the claimed subject matter.

DEFINITIONS

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| BDO | 1,4-butanediol |
| HBA | 4-hydroxybutyraldehyde |
| HMPA | 3-hydroxy-2-methylpropionaldehyde |
| PA | propionaldehyde |
| MPD | 2-Methyl-1,3-propanediol |
| GC | Gas chromatography |

DESCRIPTION OF EMBODIMENTS OF THE DISCLOSURE

The present disclosure is directed to an improved method of forming 1,4-butanediol (BDO). The improvement includes the use of methylcyclohexane as a reaction solvent to increase the efficiency of the hydroformylation of allyl alcohol, the subsequent water extraction of the hydroxyaldehyde products, and the hydrogenation of the extracted hydroxyaldehyde products to alcohols.

Previous methods of hydroformylating allyl alcohol utilized organic solvents such as toluene, cyclohexane, methyl t-butyl ether, and mixtures thereof as the reaction solvent in the presence of a catalyst system comprising rhodium complex and a substituted or unsubstituted diphosphine ligand. This combination of reaction solvent and catalyst system allowed for a much higher yield of 4-hydroxybutyraldehyde (HBA), compared to 3-hydroxy-2-methylpropionaldehyde (HMPA), leading to higher yields of BDO. However, these reaction solvents are difficult to separate from the hydroxyaldehyde products during the subsequent water extraction process, leading to a decrease in the efficiency of both the hydroformylation process and the subsequent hydrogenation.

Specifically, during the water extraction step, HBA and HMPA remain dissolved in the aqueous phase and are separated from the organic reaction solvent/catalyst phase. However, if the water phase and reaction solvent are slightly miscible, it is difficult to completely separate the two phases.

Some of the water will then be carried over with the recycled catalyst system and decrease the efficiency of the hydroformylation process. Some of the organic reaction solvent(s) are carried over into the hydrogenation process, where they can deactivate the hydrogenation catalyst. Additionally, not all of the hydroxyaldehyde products partition into the water phase, resulting in product losses.

In the presently disclosed method, methylcyclohexane is used as the reaction solvent. Methylcyclohexane was unexpectedly found to increase the reaction rate of the hydroformylation process while also improving the subsequent water extraction and hydrogenation processes, compared to the traditional organic reaction solvents. These unexpected improvements lead to a more cost-effective process due to decreases in the amount of the catalyst needed for the hydroformylation process, less water for the extraction process, and overall less energy consumption.

In more detail, methylcyclohexane was able to increase the hydroformylation reaction rate by at least about 30%, compared to reaction solvents that have previously been used in the hydroformylation of allyl alcohol. Further, the methylcyclohexane was unexpectedly found to not only be immiscible with water, but also mostly immiscible the hydroxyaldehyde products. Thus, more of the hydroxyaldehyde products partitioning into the water phase while the methylcyclohexane phase floats on top of the water during the extraction process. This results in a better separation and less water being required. Additionally, there is less carry-over for the remaining processes. Little to no water ends up being carried over with the recycle catalyst system, increasing the efficiency of the hydroformylation reaction. There is also less methylcyclohexane being carried over into the hydrogenation reactor, thus reducing the deactivation of the hydrogenation catalyst.

The remaining aspects of the hydroformylation, extraction, and hydrogenation processes can be the same as those known in the art.

Hydroformylation:

The presently described process can be carried out in either batch or continuous manner and is especially suited for continuous operation. Typical reaction conditions for the hydroformylation are mild to favor the formation of the linear 4-hydroxybutyraldehyde (HBA) rather than branched 3-hydroxy-2-methylpropionaldehyde (HMPA) co-product.

In some embodiments, the reaction conditions are in the range of from about 20 to 120° C. and pressures of from about 20 psig (~0.14 MPa) to 600 psig (~4.14 MPa). In other embodiments, the reaction conditions are in the range of about 45 to 85° C. and 30 psig (~0.21 MPa) to 400 psig (~2.76 MPa); alternatively, the reaction conditions are in the range of about 50 to 80° C. and 40 psig (~0.28 MPa) to 300 psig (~2.07 MPa). In yet other embodiments, the reaction conditions are in the range of about 65° C. to about 85° C. and a pressure of about 200 psig (~1.37 MPa).

The catalyst system used in the presently described methods comprises a rhodium complex and a substituted or unsubstituted diphosphine ligand.

In some embodiments, the diphosphine ligand is a trans-1,2-bis(bis(3,5-di-n-alkylphenyl)phosphinomethyl)-cyclobutane, which has the general formula:

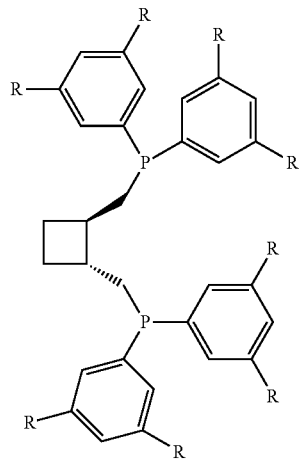

wherein R is an n-alkyl group such as methyl, ethyl, or propyl.

In some embodiments, the disphosphine ligand is trans-1,2-bis(bis(3,5-di-methylphenyl)phosphinomethyl)-cyclobutane or trans-1,2-bis(bis(3,4,5-tri-methylphenl)phosphinomethyl)-cyclobutane.

The trans-1,2-bis(bis(3,5-di-n-alkylphenyl)phosphinomethyl)cyclobutene or trans-1,2-bis(bis(3,4,5-tri-methylphenyl)phosphinomethyl)-cyclobutane may be prepared by any possible method. For example, it may be prepared by the reaction of trans-1,2-cyclobutanedimethanol, bis(toluenesulfonate) with lithium di(3,5-di-n-alkylphenyl)phosphine or lithium di(3,4,5-di-n-alkylphenyl)phosphine.

In other embodiments, the diphosphine ligand is a 4,5-bis(di-n-alkylphosphino)xanthene, which has the general formula:

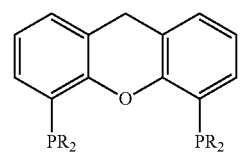

wherein R is an n-alkyl group and any of the ring carbons may be substituted or unsubstituted. The R groups may be the same or are different, but preferably are the same. In some embodiments, the R group is a $C_1$-$C_6$n-alkyl group, such as methyl, ethyl, or n-propyl.

In some embodiments, the disphosphine ligand is a 9,9-dimethyl-4,5-bis(di-n-alkylphosphino)xanthene. Alternatively, the disphosphine ligand is 9,9-dimethyl-4,5-bis(dimethylphosphino)xanthene or 9,9-dimethyl-4,5-bis(diethylphosphino)xanthene.

The 4,5-bis(di-n-alkylphosphino)xanthene may be prepared by any possible method. For example, it may be prepared by the reaction of a 4,5-dilithiumxanthene with a chloro(di-n-alkyl)phosphine.

In yet other embodiments, the diphosphine ligand is a 2,3-O-isopropylidene-2,3-dihydroxy-1,4-bis[bis(3,5-di-n-alkylphenyl)phosphino]-butane, which has the general formula:

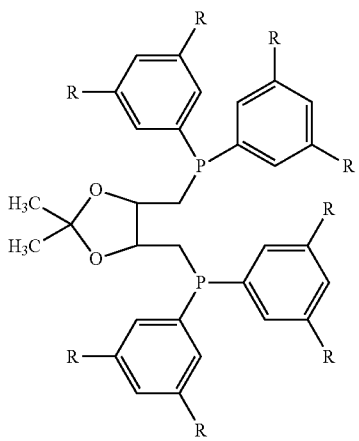

wherein R is a proton (DIOP) or is an n-alkyl group such as methyl, ethyl, or propyl.

In some embodiments, the disphosphine ligand is 2,3-O-isopropylidene-2,3-dihydroxy-1,4-bis[bis(3,5-dimethylphenyl)phosphino]butane or 2,3-O-isopropylidene-2,3-dihydroxy-1,4-bis(3,5-diethylphenyl)phosphino]butane.

The 2,3-O-isopropylidene-2,3-dihydroxy-1,4-bis[bis(3,5-di-n-alkylphenyl)phosphino]-butane may be prepared by any possible method. For instance, it may be prepared by the reaction of 2,2-dimethyl-4,5-bis[(toluenesulfonyloxymethyl)methyl]-1,3-dioxolane with lithium di(3,5-di-n-alkylphenyl)-phosphine.

The catalyst system also comprises a rhodium complex. Exemplary rhodium complexes contain rhodium attached to ligand groups. The rhodium complex is preferably soluble in the methylcyclohexane. There are no particular restrictions regarding the choice of ligands attached to the rhodium complex. For example, the ligands include hydrides, carbonyl, substituted and unsubstituted cyclopentadienyls, 2,4-alkanedionates, trialkyl or triaryl phosphines, diphosphines, and mixtures thereof. In some embodiments, the ligands include carbonyl, acetylacetonate (2,4-pentanedionate), triphenylphosphine, and mixtures thereof. In other embodiments, the rhodium complexes include (acetylacetonato)dicarbonyl rhodium and tris(triphenylphosphine)rhodium carbonyl hydride.

The molar ratio of the diphosphine ligand:rhodium complex is in the range of 0.5:1 to 5:1. In some embodiments, the molar ratio of the diphosphine ligand:rhodium complex is in the range of 0.5:1 to 2.5:1. In some embodiments, the molar ratio of the diphosphine ligand:rhodium complex is in the range of 0.5:1 to 1.5:1. In some embodiments, the molar ratio of the diphosphine ligand:rhodium complex is in the range of 1:1 to 4.5:1. In some embodiments, the molar ratio of the diphosphine ligand:rhodium complex is in the range of 1:1 to 3:1. In some embodiments, the molar ratio of the diphosphine ligand:rhodium complex is in the range of 2:1 to 5:1. In some embodiments, the molar ratio of the diphosphine ligand:rhodium complex is in the range of 3:1 to 5:1. The rhodium complex can be pre-associated with the diphosphine ligand prior to use in the hydroformylation reaction such that the diphosphine ligand forms part of the rhodium complex, or it can be added separately. However, in some embodiments, it is preferable to add the rhodium complex separately from the diphosphine ligand.

Although not necessary, the catalyst system may additionally comprise a monophosphine compound. The monophosphine compound is in addition to any phosphine ligand that may be associated with the rhodium complex. The monophosphine compound is a trisubstituted phosphine that is represented by the formula $(R^1)_3P$, wherein $R^1$ is an aryl or alkyl group. Exemplary aliphatic $R^1$ groups include methyl, ethyl, n-butyl, sec-butyl, octyl, and decyl, and exemplary aromatic $R^1$ groups include phenyl, tolyl, and naphthyl. The $R^1$ groups may be the same or are different, but preferably are the same. In some embodiments, the monophosphine is a trisubstituted aryl phosphine. Alternatively, the monophosphine is triphenyl phosphine or tritolyl phosphine.

In addition to the reaction solvent and catalyst system, the hydroformylation process also combines the ally alcohol substrate with carbon monoxide (CO) and hydrogen ($H_2$). The molar ratio of $CO:H_2$ is often about 1:1, although the ratio can vary considerably. The partial pressure of CO is within the range of 5 to 100 psig. The partial pressure of hydrogen is within the range of 40 psig (~0.28 MPa) to 200 psig (~1.38 MPa). The reaction is conducted at these conditions until a predominance of the allyl alcohol has reacted, e.g. 60 to 99.9%, the products being largely HBA with some branched reaction products. The amount of reaction time is not critical, but usually a reaction time of 0.5 to 4 hours is adequate.

The allyl alcohol starting concentration on a methylcyclohexane reaction solvent to feed basis is in the range of about 5 to 40 percent by weight in the methylcyclohexane. Alternatively, a lower concentration in the range of 5 to 10 percent by weight in the methylcyclohexane may be used. In yet another alternative, the allyl alcohol starting concentration is in the range of 15 to 30 percent by weight in the methylcyclohexane; or 25 to 40 percent by weight in the methylcyclohexane.

The hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference. In some embodiments, the liquid phase hydrogen:carbon monoxide molar ratio is in the range of from 10:1 to about 1:2, or from 5:1 to about 1:2.

Following the hydroformylation process, the HBA product is separated from the solvent and catalyst system by water extraction in an extraction vessel.

Water Extraction:

Water extraction methods are well known in the art and can be effected by any suitable means, such as mixer-settlers, packed or trayed extraction columns, rotating disk contactors, or passed to a settling tank for resolution of the mixture into aqueous and organic phases.

As explained above, the hydroxyaldehyde products such as HBA and HMPA are not soluble in the methylcyclohexane reaction solvent. This allows the hydroxyaldehyde products to easily partition into the water (aqueous) phase where they are more soluble. Further, the methylcyclohexane is immiscible in the water phase, allowing it to float on top of the water and be separated. The combination of both the immiscibility of the methylcyclohexane and the water phase, and the immiscibility of the methylcyclohexane and the hydroxyaldehyde products facilitates an easier separation process. p In direct contrast to their immiscibility with methylcyclohexane, the hydroxyaldehyde products are completely miscible with other solvents such as toluene. Like methylcyclohexane, the toluene is immiscible in the water phase and floats on top. However, the miscibility of the hydroxyaldehyde products in toluene makes their extraction therefrom more challenging. While extraction is efficient enough to allow process, some toluene is entrained in the aqueous hydroxyaldehyde product extract and some water is carried over in the recycled toluene catalyst solution. This leads to catalyst loss and/or deactivation as well as increases in the cost of the hydroformylation process.

Hydrogenation:

The HBA (and any HMPA) reaction product is subjected to an additional step of hydrogenating the 4-hydroxybutyraldehyde in the presence of a hydrogenation catalyst to produce 1,4-butanediol (BDO). Hydrogen is added to the reaction vessel for the hydrogenation. Exemplary hydrogenation catalysts include any Group VIII metal, such as nickel, cobalt, ruthenium, platinum, and palladium, as well as copper, zinc and chromium and mixtures and alloys thereof. Especially preferred are nickel catalysts. Most preferred are Raney®-type nickel and fixed bed nickel catalysts.

Any known hydrogenation conditions can be used. In some embodiments, the hydrogenation reaction conditions are in the range of from 60 to 200° C. and pressures of from 200 psig (~1.38 MPa) to 1000 psig (~6.89 MPa). In other embodiments, the hydrogenation reaction conditions are in the range of from 80 to 140° C. and 300 psig (~2.07 MPa) to 1000 psig (~6.89 MPa). The hydrogenation reaction times are between about 1 to about 10 hours.

Using the above-described methods, the production of BDO is improved because, without wishing to be bound to theory, the methylcyclohexane reaction solvent increases the reaction rate of the hydroformylation process while reducing the carryover of water from the extraction process. Additionally, the immiscibility of the methylcyclohexane and water leads to improved separation compared to traditionally hydroformylation reaction solvents. This reduces the amount of water needed for the extraction and reduces the amount of methylcyclohexane present during the subsequent hydrogenation process. Thus, the use of a methylcyclohexane reaction solvent leads to a more cost-effective method for generating greater amounts of BDO.

EXAMPLE

The following is included to demonstrate embodiments of the appended claims using the above described hydroformylation process. This example is intended to be illustrative only, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

In this example, different reaction solvents were combined with the catalyst system for the hydroformylation of allyl alcohol. Each batch reaction was performed at 65° C. and 200 psig pressure with a Rh-ligand A catalyst system, wherein ligand A is a trans-1,2-bis(bis(3,5-di-n-methylphenyl)phosphinomethyl)-cyclobutane. The molar composition for the catalyst system was [Rh]:[ligand A]=1:2. The amount of the rhodium in each reaction solvent was [Rh]=4.3×10$^{-5}$ moles. For each reaction, the HBA and HMPA were analyzed using gas chromatography (GC). A hydrogenation step was not performed because the conversion from hydroxyaldehyde products to diols is readily accomplished with greater than 99% conversion and selectivity. Thus, the ratio of HBA and HMPA generated in the hydroformylation process were used to project the amount of BDO and MPD that would form after a hydrogenation process. Table 1 displays the results for each reaction.

TABLE 1

Comparison of solvents

| Reaction Solvent | BDO | MPD | C3 | L:B | Rate comparison |
| --- | --- | --- | --- | --- | --- |
| Toluene | 89.6 | 9.3 | 0.12 | 9.64 | |
| Methylcyclohexane | 89.7 | 9.4 | 0.08 | 9.57 | 1.36× rate in toluene. |
| Ethyl cyclohexane | 89.4 | 9.5 | 0.09 | 9.6 | 1.03× rate in toluene |
| Cyclohexane | 90.2 | 9.1 | 0.08 | 9.88 | 1.2× rate in toluene |
| Ethylbenzene | 89.5 | 9.0 | 0.11 | 9.89 | ~0.93× rate in toluene |
| Cyclohexene | 70 | 29 | 0.32 | 2.4 | 0.66× rate in toluene |
| m-Xylene | 88.6 | 9.3 | 0.14 | 9.5 | Similar rate to toluene |
| o-Xylene | 89.7 | 9.3 | 0.11 | 9.7 | Similar rate to toluene |
| p-Xylene | 90.1 | 9.3 | 0.12 | 9.7 | Similar rate to toluene |

L:B = ratio of linear HBA to branched HMPA

Toluene was used as the baseline comparison for the rate of reaction for the other reaction solvents. Many of these reaction solvents have been used in the hydroformylation processes before and have a rate similar to toluene. However, changing the reaction solvent to methylcyclohexane unexpectedly resulted in a large increase in the reaction rate, as shown in Table 1. Methylcyclohexane increased the rate of the reaction by 36%, which indicates that less rhodium metal could be used in the catalyst system. This would significantly increase cost savings for the HBA production process.

While cyclohexane also increased the rate, compared with toluene, by about 20%, it was noted that separating this solvent during the water extraction step would be more difficult than methylcyclohexane. Cyclohexane has some miscibility in the water phase, making it difficult to separate from the water. This would result in water being carried over in the cyclohexane catalyst system as well as catalyst solution being entrained in the aqueous extract resulting in catalyst loss and/or deactivation.

In contrast, the hydroxyaldehyde products were not soluble in the methylcyclohexane. In fact, during subsequent gas chromatography (GC) analysis of each reaction product, ethanol had to be added to the methylcyclohexane reaction product sample to form a single-phase solution for accurate analysis. Such a step was not needed for the other reaction solvents. This insolubility allows for the hydroxyaldehyde products to easily partition into the water phase during the water extraction step. Further, the methylcyclohexane is immiscible with the water phase, allowing it to separate and float above the water. This is a better separation than that seen with the other reaction solvents in Table 1, meaning that less water would be needed for the extraction step. Additionally, little to no water carry over with the catalyst system, again decreasing the cost of the hydroformylation process.

In addition to the increase in reaction rate and improved separation, the use of methylcyclohexane also reduced the formation of unwanted C3 side products. Formation of the C3 byproducts effectively represents another yield loss in the process which can have a severe adverse effect on the process economics. The use of methylcyclohexane provided one of the lowest C3 selectivities.

The amount of BDO and MPD in Table 1 were projected from the ratio of linear HBA to branched HMPA (L:B). The use of methylcyclohexane did not substantially affect the ability to achieve a high yield of HBA compared to HMPA, thus it will not negatively affect the projected amounts of BDO and MPD. As seen in Table 1, the projected values are similar to those seen with other reaction solvents so there is no efficiency loss in the hydroformylation reaction when methylcyclohexane is used instead other known reaction solvents.

Thus, the use of methylcyclohexane as the reaction solvent in the catalyst system provides a more economically attractive production method for the hydroformylation of allyl alcohol. The use of methylcyclohexane unexpectedly increases the rate of reaction, which reduces the amount of rhodium needed in the catalyst and thus reduces the cost of the process. Further, the reaction products insoluble in methylcyclohexane, and methylcyclohexane immiscibility with the water phase improves the separation process. This not only reduces the amount of water carried over alongside the recycled solvent/catalyst system into the hydroformylation reactor, it increases the recovery of the desired reaction products.

The following references are incorporated by reference in their entirety.

U.S. Pat. No. 7,612,241
U.S. Pat. No. 7,279,606
U.S. Pat. No. 7,271,295

ADDITIONAL DISCLOSURE

Embodiments disclosed herein include:

A: a process to produce 4-hydroxybutyraldehyde comprising reacting allyl alcohol with carbon monoxide and hydrogen in the presence of a methylcyclohexane reaction solvent and a catalyst system comprising a rhodium complex and a substituted or unsubstituted diphosphine ligand.

Embodiment A may include one or more of the following additional elements:

Element 1: wherein the diphosphine ligand is trans-1,2-bis(bis(3,5-di-n-alkylphenyl)phosphinomethyl)-cyclobutane, trans-1,2-bis(bis(3,4,5-di-n-alkylphenyl)phosphinomethyl)-cyclobutane, 4,5-bis(di-n-alkylphosphino)xanthene, or 2,3-O-isopropylidene-2,3-dihydroxy-1,4-bis [bis(3,5-di-n-alkylphenyl)phosphino]-butane, wherein the n-alkyl is a methyl, ethyl, or propyl group. Element 2: wherein the trans-1,2-bis(bis(3,5-di-n-alkylphenyl)phosphinomethyl)-cyclobutane is trans-1,2-bis(bis(3,5-di-methylphenyl)phosphinomethyl)-cyclobutane. Element 3: wherein the trans-1,2-bis(bis(3,5-di-n-alkylphenyl)phosphinomethyl)-cyclobutane is trans-1,2-bis(bis(3,5-di-ethylphenyl)phosphinomethyl)-cyclobutane. Element 4: wherein the 4,5-bis(di-n-alkylphosphino)xanthene is 9,9-dimethyl-4,5-bis(dimethylphosphino)xanthene or 9,9-dimethyl-4,5-bis(diethylphosphino)xanthene. Element 5: wherein the 2,3-O-isopropylidene-2,3-dihydroxy-1,4-bis[bis(3,5-di-n-alkylphenyl)phosphino]-butane is 2,3-O-isopropylidene-2,3-dihydroxy-1,4-bis[bis(3,5-dimethylphenyl)phosphino]butane or 2,3-O-isopropylidene-2,3-dihydroxy-1,4-bis[bis(3,5-diethylphenyl)phosphino]butane. Element 6: wherein the rhodium complex comprises rhodium and one or more ligands selected from the group consisting of hydride, carbonyl, trialkyl or triaryl phosphines, diphosphines, cyclopentadienyls, 2,4-alkanedionates, and mixtures thereof. Element 7: wherein the reaction is performed at a temperature within the range of about 45° C. to about 85° C. and a pressure within the range of about 30 psig (~0.21 MPa) to about 400 psig (~2.76 MPa). Element 8: wherein the reaction is performed at a temperature within the range of about 65° C. to about 85° C. and a pressure of about 200 psig (~1.37 MPa). Element 9: wherein the catalyst system further comprises a monophosphine compound. Element 10: wherein the monophosphine compound is triphenylphosphine. Element 11: wherein the concentration of carbon monoxide in the liquid phase is maintained above 4 mmols/liter (0.004 M). Element 12: further comprising hydrogenating the 4-hydroxybutyraldehyde in the presence of a hydrogenation catalyst to form 1,4-butanediol. Element 13: wherein the hydrogenation catalyst is a nickel catalyst. Element 14: wherein the concentration of carbon monoxide in the liquid phase if maintained in the range of from about 2 mmols/liter (0.002 M) to about 10 mmols/liter (0.010 M). Element 15: wherein the concentration of carbon monoxide in the liquid phase is maintained in the range of from about 3 mmols/liter (0.003 M) to about 6 mmols/liter (0.006M). Element 16: wherein the concentration of carbon monoxide in the liquid phase is maintained in the range of from about 4 mmols/liter (0.004M) to about 8 mmols/liter (0.008 M). Element 17: wherein the concentration of carbon monoxide in the liquid phase is maintained in the range of from about 4 mmols/liter (0.004M) to about 25 mmols/liter (0.025 M). Element 18: wherein the concentration of carbon monoxide in the liquid phase is maintained in the range of from about 4 mmols/liter (0.004M) to about 50 mmols/liter (0.050 M). Element 19: wherein the concentration of carbon monoxide in the liquid phase is maintained in the range of from about 4 mmols/liter (0.004M) to about 100 mmols/liter (0.100 M).

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is present, or alternatively, the element is not present, both alternatives being within the scope of the claim. In the claims, means-plus-function clauses are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words "means for" together with an associated function.

Numbers and ranges disclosed above may vary by some amount. Whenever a numerical range with a lower limit and an upper limit is disclosed, any number and any included range falling within the range is specifically disclosed. In particular, each range of values (of the form, "from about a to about b," or, equivalently, "from approximately a to b," or, equivalently, "from approximately a-b") disclosed herein is to be understood to set forth each number and range encompassed within the broader range of values. Also, the terms in the claims have their plain, ordinary meaning unless otherwise explicitly and unambiguously defined by the patentee. If there is any conflict in the usages of a word or term in this specification and one or more patent or other documents, the definitions that are consistent with this specification should be adopted.

Accordingly, the scope of protection is not limited by the description set out above but is only limited by the claims which follow, such scope including equivalents of the subject matter of the claims.

What is claimed is:

1. A process to produce 4-hydroxybutyraldehyde comprising reacting allyl alcohol with carbon monoxide and hydrogen in the presence of a methylcyclohexane reaction solvent and a catalyst system comprising a rhodium complex and a substituted or unsubstituted diphosphine ligand.

2. The process of claim 1, wherein the diphosphine ligand is trans-1,2-bis(bis(3,5-di-n-alkylphenyl)phosphinomethyl)-cyclobutane, trans-1,2-bis(bis(3,4,5-di-n-alkylphenyl)phosphinomethyl)-cyclobutane, 4,5-bis(di-n-alkylphosphino)xanthene, or 2,3-O-isopropylidene-2,3-dihydroxy- 1,4-bis[bis(3,5-di-n-alkylphenyl)phosphino]-butane, wherein the n-alkyl is a methyl, ethyl, or propyl group.

3. The process of claim 2, wherein said trans-1,2-bis(bis(3,5-di-n-alkylphenyl)phosphinomethyl)-cyclobutane is trans-1,2-bis(bis(3,5-di-methylphenyl)phosphinomethyl)-cyclobutane.

4. The process of claim 2, wherein said trans-1,2-bis(bis(3,5-di-n-alkylphenyl)phosphinomethyl)-cyclobutane is trans-1,2-bis(bis(3,5-di-ethylphenyl)phosphinomethyl)-cyclobutane.

5. The process of claim 2, wherein said 4,5-bis(di-n-alkylphosphino)xanthene is 9,9-dimethyl-4,5-bis(dimethylphosphino)xanthene or 9,9-dimethyl-4,5-bis(diethylphosphino)xanthene.

6. The process of claim 2, wherein said 2,3-O-isopropylidene-2,3-dihydroxy-1,4-bis[bis(3,5-di-n-alkylphenyl)phosphino]-butane is 2,3-O-isopropylidene-2,3-dihydroxy-1,4-bis[bis(3,5-dimethylphenyl)phosphino]butane or 2,3-O-isopropylidene-2,3-dihydroxy-1,4-bis[bis(3,5-diethylphenyl)phosphino]butane.

7. The process of claim 1, wherein the rhodium complex comprises rhodium and one or more ligands selected from the group consisting of hydride, carbonyl, trialkyl or triaryl phosphines, diphosphines, cyclopentadienyls, 2,4-alkanedionates, and mixtures thereof.

8. The process of claim 1, wherein the reaction is performed at a temperature within the range of about 20° C. to about 120° C. and a pressure within the range of about 20 psig (~0.14 MPa) to about 600 psig (~4.14 MPa).

9. The process of claim 1, wherein the reaction is performed at a temperature within the range of about 65° C. to about 85° C. and a pressure of about 200 psig (~1.37 MPa).

10. The process of claim 1, wherein the catalyst system further comprises a monophosphine compound.

11. The process of claim 10, wherein the monophosphine compound is triphenylphosphine.

12. The process of claim 1, wherein the concentration of carbon monoxide in the liquid phase is maintained above 4 mmols/liter (0.004 M).

13. The process of claim 1, further comprising hydrogenating the 4-hydroxybutyraldehyde in the presence of a hydrogenation catalyst to form 1,4-butanediol.

14. The process of claim 13, wherein the hydrogenation catalyst is a nickel catalyst.

15. The process of claim 1 wherein the concentration of carbon monoxide in the liquid phase is maintained in the range of from about 4 mmols/liter (0.004M) to about 100 mmols/liter (0.100 M).

* * * * *